(12) United States Patent
Ding

(10) Patent No.: US 10,144,208 B2
(45) Date of Patent: Dec. 4, 2018

(54) METHOD FOR DETECTING CHARACTERISTIC OF FORMING MATERIAL AND THREE-DIMENSIONAL PRINTING APPARATUS

(71) Applicants: XYZprinting, Inc., New Taipei (TW); Kinpo Electronics, Inc., New Taipei (TW); Cal-Comp Electronics & Communications Company Limited, New Taipei (TW)

(72) Inventor: Ming-Hsiung Ding, New Taipei (TW)

(73) Assignees: XYZprinting, Inc., New Taipei (TW); Kinpo Electronics, Inc., New Taipei (TW); Cal-Comp Electronics & Communications Company Limited, New Taipei (TW)

( * ) Notice: Subject to any disclaimer, the term of this patent is extended or adjusted under 35 U.S.C. 154(b) by 973 days.

(21) Appl. No.: 14/454,735

(22) Filed: Aug. 8, 2014

(65) Prior Publication Data

US 2015/0321421 A1 Nov. 12, 2015

(30) Foreign Application Priority Data

May 12, 2014 (TW) .............................. 103116731 A

(51) Int. Cl.
*B29C 67/00* (2017.01)
*B33Y 50/02* (2015.01)
(Continued)

(52) U.S. Cl.
CPC ............ *B33Y 50/02* (2014.12); *B29C 64/129* (2017.08); *B29C 64/135* (2017.08);
(Continued)

(58) Field of Classification Search
CPC . B29C 67/0066; B29C 67/0088; B33Y 50/02; B33Y 10/00; B33Y 30/00; G01N 2021/551; G01N 21/55
(Continued)

(56) References Cited

U.S. PATENT DOCUMENTS

| 5,174,931 A | * | 12/1992 | Almquist | ................ B29C 41/12 118/100 |
| 5,688,464 A | * | 11/1997 | Jacobs | .................... B29C 41/12 264/308 |

(Continued)

FOREIGN PATENT DOCUMENTS

| CN | 101918198 | 12/2010 |
| JP | 4140891 | 8/2008 |

OTHER PUBLICATIONS

"Office Action of China Counterpart Application", dated Nov. 30, 2016, p. 1-p. 8.

(Continued)

*Primary Examiner* — Christina A Johnson
*Assistant Examiner* — Xue H Liu
(74) *Attorney, Agent, or Firm* — JCIPRNET

(57) ABSTRACT

A method for detecting a characteristic of a forming material and a three-dimensional printing apparatus are provided. The three-dimensional printing apparatus includes a tank filled with a liquid forming material, and the method includes the following. The tank is controlled to swing to cause a wave motion on a liquid surface of the liquid forming material. The wave motion of the liquid forming material is detected to obtain detection waveform information. The detection waveform information and sample waveform information are compared with each other to obtain a characteristic comparison result. A predefined operation is executed according to the characteristic comparison result.

9 Claims, 8 Drawing Sheets

(51) Int. Cl.
  *G01N 21/55* (2014.01)
  *B29C 64/135* (2017.01)
  *B29C 64/129* (2017.01)
  *B29C 64/386* (2017.01)
  *B29K 105/00* (2006.01)
  *B33Y 10/00* (2015.01)
  *B33Y 30/00* (2015.01)

(52) U.S. Cl.
  CPC ........... *B29C 64/386* (2017.08); *G01N 21/55* (2013.01); *B29K 2105/0058* (2013.01); *B33Y 10/00* (2014.12); *B33Y 30/00* (2014.12); *G01N 2021/551* (2013.01)

(58) Field of Classification Search
  USPC .......................................................... 264/401
  See application file for complete search history.

(56) References Cited

U.S. PATENT DOCUMENTS

| | | | |
|---|---|---|---|
| 2009/0020901 A1* | 1/2009 | Schillen | B29C 67/0051 264/31 |
| 2009/0051935 A1 | 2/2009 | Cooper | |
| 2010/0156003 A1 | 6/2010 | Wahlstrom | |
| 2012/0195994 A1* | 8/2012 | El-Siblani | B29C 67/007 425/174.4 |
| 2012/0321759 A1* | 12/2012 | Marinkovich | A61B 5/0531 426/231 |

OTHER PUBLICATIONS

"Office Action of Taiwan Counterpart Application", dated Dec. 8, 2016, p. 1-p. 10.

\* cited by examiner

METHOD FOR DETECTING CHARACTERISTIC OF FORMING MATERIAL AND THREE-DIMENSIONAL PRINTING APPARATUS

CROSS-REFERENCE TO RELATED APPLICATION

This application claims the priority benefit of Taiwan application serial no. 103116731, filed on May 12, 2014. The entirety of the above-mentioned patent application is hereby incorporated by reference herein and made a part of this specification.

BACKGROUND

Technical Field

The technical field relates to a method for detecting a printing status and more particularly relates to a method for detecting a characteristic of a forming material and a three-dimensional printing apparatus.

Description of Related Art

As technology advanced in the recent years, many methods that utilize additive manufacturing technology (e.g. layer-by-layer model construction) to build three-dimensional (3D) physical models have been proposed. Generally speaking, the additive manufacturing technology is to transfer data of the design of a 3D model, which is constructed by software, such as computer aided design (CAD), to multiple thin (quasi-two-dimensional) cross-sectional layers that are stacked in sequence. In the meantime, many techniques for forming thin cross-sectional layers are also proposed. For example, a printing module of a printing apparatus is usually configured to move above a base along an XY plane according to spatial coordinates XYZ constructed according to the design data of the 3D model, so as to use a construction material to form shapes of the cross-sectional layers correctly. By moving the printing module along the Z axis layer by layer, multiple cross-sectional layers can be gradually stacked along the Z axis, and while the construction material is cured layer by layer, a 3D object is formed.

Take the technique of forming the 3D object by curing the construction material with a light source for example, the printing module is adapted to be immersed in a liquid forming material contained in a tank, and a light source module is used to irradiate the liquid forming material, used as the construction material, on the XY plane, so as to cure the liquid forming material and stack it on a forming platform of the printing module. Accordingly, by moving the forming platforms of the printing module layer by layer along the Z axis, the liquid forming material can be gradually cured and stacked to form the 3D object. However, it should be noted that different liquid forming materials may have different material characteristics. For this reason, correct control printing parameters need to be set to the three-dimensional printing apparatus according to the type of the liquid forming material. If the control printing parameters set to the three-dimensional printing apparatus do not match the type of the liquid forming material, printing failure or poor printing quality may occur. In addition, in the process of stacking the forming material layer by layer to form the 3D object, the material characteristic of the liquid forming material may change with time and cause the control printing parameters of the three-dimensional printing apparatus to fail to match the type of the liquid forming material. Therefore, how to improve 3D printing speed and quality is still an important issue in this field.

SUMMARY

One of the exemplary embodiments provides a method for detecting a characteristic of a forming material and a three-dimensional printing apparatus, wherein the three-dimensional printing apparatus is controlled instantly to execute a corresponding operation by detecting a material characteristic of a liquid forming material, so as to achieve favorable printing quality.

One of exemplary embodiments provides a method for detecting a characteristic of a forming material, adapted for a three-dimensional printing apparatus. The three-dimensional printing apparatus includes a tank filled with a liquid forming material, and the method includes the following. The tank is controlled to swingswing, so as to cause a wave motion on a liquid surface of the liquid forming material. The wave motion of the liquid forming material is detected to obtain detection waveform information. The detection waveform information and sample waveform information are compared with each other to obtain a characteristic comparison result in association with the liquid forming material. A predefined operation is executed according to the characteristic comparison result.

One of exemplary embodiments provides a three-dimensional printing apparatus, which includes a tank, a forming platform, a light source, a detection unit, and a control unit. The tank is filled with a liquid forming material, and the forming platform is movably disposed above the tank. The light source is disposed under the tank for irradiating the liquid forming material. The detection unit is disposed at a side of the tank for detecting a wave motion on a liquid surface of the liquid forming material. The control unit is coupled to the detection unit and the forming platform for controlling the tank to swingswing, so as to cause the wave motion on the liquid surface of the liquid forming material. The control unit is configured to detect the wave motion of the liquid forming material through the detection unit, so as to obtain detection waveform information. The control unit is configured to compare the detection waveform information with sample waveform information to obtain a characteristic comparison result in association with the liquid forming material. The control unit is configured to execute a predefined operation according to the characteristic comparison result.

Based on the above, in the embodiments of the disclosure, the three-dimensional printing apparatus includes a floating module that is adapted to float on the liquid surface of the liquid forming material. Accordingly, the three-dimensional printing apparatus is capable of detecting the wave motion on the liquid surface of the liquid forming material through the floating module, thereby obtaining the detection waveform information indicative of the current material characteristic. Further, the three-dimensional printing apparatus obtains the characteristic comparison result by comparing the detection waveform information with the sample waveform information in the database, and adjusts the control parameter for printing a three-dimensional object based on the characteristic comparison result, so as to improve the quality of three-dimensional printing. In addition to the above, the three-dimensional printing apparatus determines whether the liquid forming material in the tank conforms to the control parameter set by the user according to the characteristic comparison material, so as to prevent printing failure.

To make the aforementioned and other features and advantages of the disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
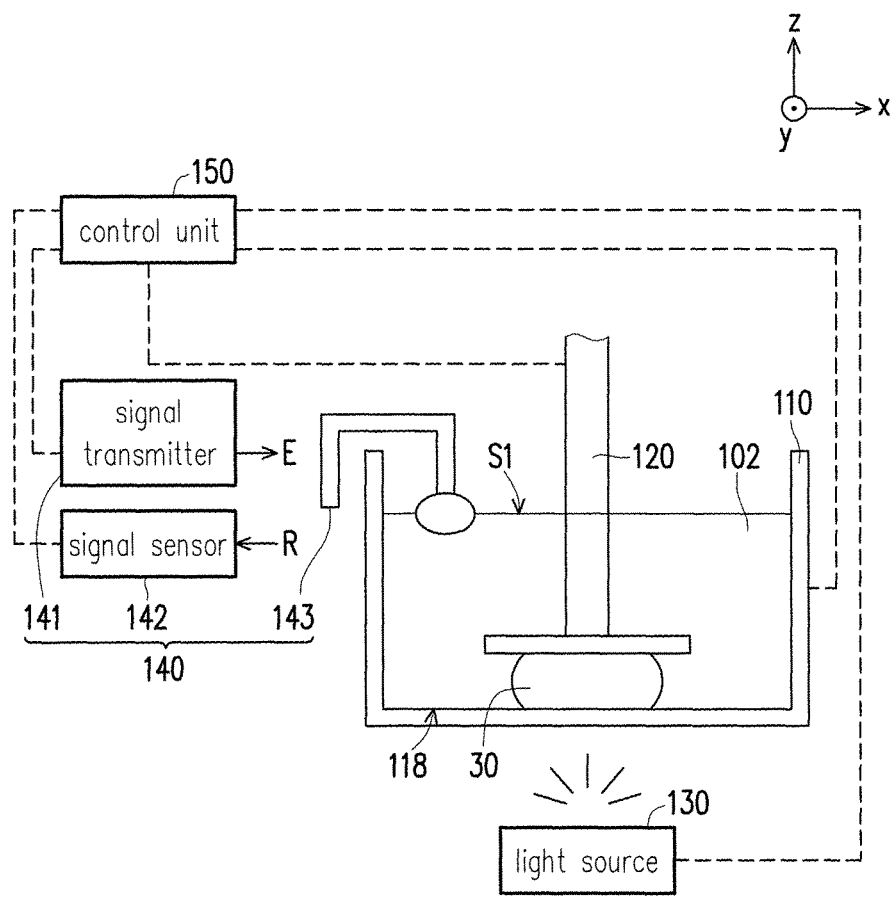
FIG. 1 is a schematic diagram illustrating a three-dimensional printing apparatus according to an exemplary embodiment.

It should be understood that the foregoing and other detailed descriptions, features, and effects are intended to be described more comprehensively by providing embodiments accompanied with drawings hereinafter. In the following embodiments, wording used to indicate directions, such as "up," "down," "front," "back," "left," and "right," merely refers to directions in the accompanying drawings. Therefore, the directional wording is used to illustrate rather than limit the disclosure. Moreover, the same or similar reference numerals represent the same or similar elements in the following embodiments.

FIG. 1 is a schematic diagram illustrating a three-dimensional printing apparatus according to an exemplary embodiment. With reference to FIG. 1, a three-dimensional printing apparatus 10 is a SL (stereolithography) printing apparatus, for example. The three-dimensional printing apparatus 10 includes a tank 110, a forming platform 120, a light source 130, a detection unit 140, and a control unit 150. Here, a Cartesian coordinate system is used to describe the components and their motions. The tank 110 is configured to be filled with a liquid forming material 102. The forming platform 120 is movably disposed above the tank 110 and adapted to be immersed in the liquid forming material 102. The light source 130 is disposed under the tank 110 for irradiating the liquid forming material 102. In this embodiment, a photosensitive resin or other suitable light-curing material is used as the liquid forming material 102. Thus, after being irradiated by the light of the light source 130, the liquid forming material 102 is cured.

The control unit 150 is coupled to the tank 110, the forming platform 120, and the light source 130 for controlling the tank 110, the forming platform 120, and the light source 130. More specifically, the three-dimensional printing apparatus 10 is adapted for fabricating a three-dimensional object 30 according to a digital three-dimensional model, wherein the digital three-dimensional model may be constructed with use of computer aided design (CAD) or animation modeling software, for example, so as to crosscut the digital three-dimensional model into a plurality of cross-sections. The three-dimensional printing apparatus 10 reads the digital three-dimensional model and prints out the three-dimensional object 30 layer by layer according to the cross-sections of the digital three-dimensional model, and the three-dimensional object 30 is obtained by using the light source 130 to irradiate and cure the liquid forming material 102 layer by layer.

To be more specific, in this embodiment, the forming platform 120 is positioned above the tank 110 and is adapted to move along an axis relative to the tank 110. As shown in FIG. 1, for example, the forming platform 120 is adapted to move along an axis Z relative to the tank 110 disposed on the XY plane and is adapted to be immersed in the liquid forming material 102 contained in the tank 110. The control unit 150 controls the forming platform 120 immersed in the liquid forming material 102 to move in a direction along the axis Z away from the light source 130, so as to cure the liquid forming material 102 layer by layer, such that the liquid forming material 102 is stacked layer by layer on the forming platform 120 to form the three-dimensional object 30.

It should be noted that the three-dimensional printing apparatus 10 further includes a detection unit 140 coupled to the control unit 150. The detection unit 140 is disposed at a side of the tank 110 for detecting a wave motion on a liquid surface S1 of the liquid forming material 102. In this embodiment, the detection unit 140 includes a signal transmitter 141, a signal sensor 142, and a floating module 143. The floating module 143 is adapted to float on the liquid surface S1 of the liquid forming material 102. Therefore, when the wave motion on the liquid surface S1 of the liquid forming material 102 is generated, the floating module 143 swings with the wave motion on the liquid surface S1. Moreover, the signal transmitter 141 transmits an output signal E to the floating module 143, and the signal sensor 142 is adapted to sense a receiving signal R in association with the output signal E. The receiving signal R may be the output signal E or a reflected signal of the output signal E according to a configuration of the signal transmitter 141 and the signal sensor 142.

Further, when the floating module 143 swings due to the wave motion on the liquid surface S1, because the signal transmitter 141 transmits the output signal E to the floating module 143, the intensity of the receiving signal R changes with the swing of the floating module 143. Based on the above, the control unit 150 detects the wave motion on the liquid surface S1 of the liquid forming material 102 according to the intensity of the receiving signal R.

It is known that the output signal E transmitted by the signal transmitter 141 and the receiving signal R sensed by the signal sensor 142 are signals of the same type. However, the output signal E and the receiving signal R may be signals that need to be transmitted through a medium or may be signals that do not need to be transmitted through a medium.

The disclosure is not intended to limit the types of the output signal E and the receiving signal R. For example, the output signal E and the receiving signal R may be light or sound waves. In other words, the disclosure is not intended to limit how the signal transmitter 141 and the signal sensor 142 are implemented. For example, the signal transmitter 141 may be a light transmitter or a sound wave transmitter. Accordingly, the signal sensor 142 may be a light sensor or a sound wave sensor.

Figure 2:
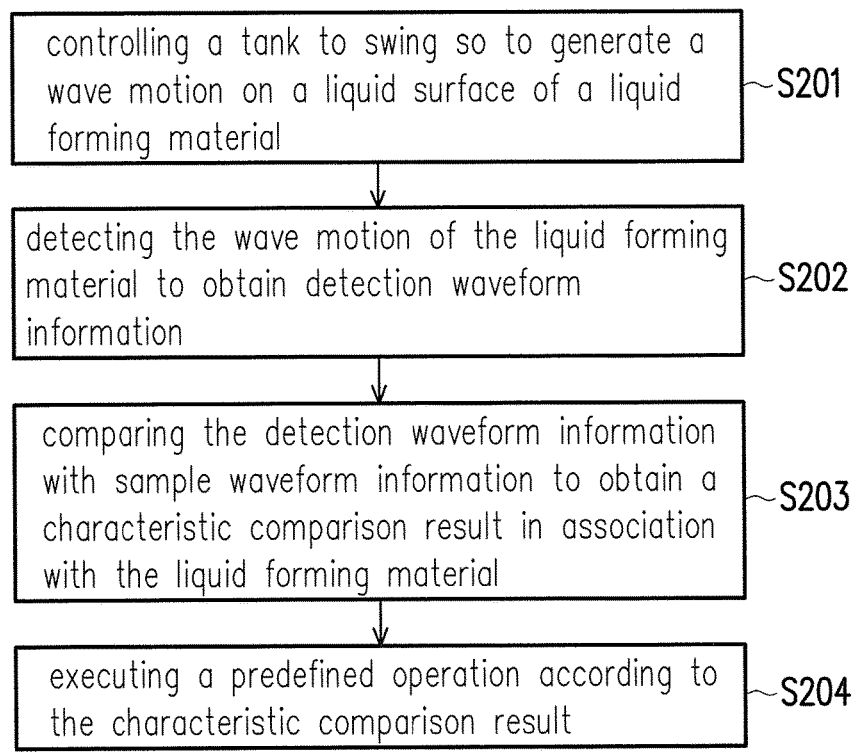
FIG. 2 is a flowchart illustrating a method for detecting a characteristic of a forming material according to an exemplary embodiment.

FIG. 2 is a flowchart illustrating a method for detecting a characteristic of a forming material according to an exemplary embodiment. The method for detecting the characteristic of the forming material in this embodiment is adapted for the three-dimensional printing apparatus 10 of FIG. 1. Steps of this embodiment are explained in detail hereinafter with reference to the components and modules of the three-dimensional printing apparatus 10. Please refer to FIG. 1 and FIG. 2.

First, in Step S201, the control unit 150 controls the tank 110 to swing, so as to generate a wave motion on the liquid surface S1 of the liquid forming material 102. In an embodiment, the control unit 150 controls the tank 110 to move, so as to cause the liquid forming material 102 that has been cured to be separated from a bottom 118 of the tank 110 and cause the tank 110 to swing thereby. More specifically, because the liquid forming material 102 is cured between the forming platform 120 and the bottom 118 of the tank 110, the cured liquid forming material 102 may adhere to the bottom 118 of the tank 110. In order to separate the cured liquid forming material 102 from the bottom 118 of the tank 110, the control unit 150 may control the tank 110 to swing or shake slightly, before controlling the forming platform 120 to rise to the next height along the axis Z and beginning light curing, so as to cause the cured liquid forming material 102 to be completely separated from the bottom 118.

In other words, when the control unit 150 controls the tank 110 to swing to separate the cured liquid forming material 102 from the bottom 118, the wave motion is generated on the liquid surface S1 of the uncured liquid forming material 102 in the tank 110. It should be noted that the aforementioned method for shaking the tank is one of the embodiments of the disclosure. The disclosure is not intended to limit the timing and method that the control unit 150 controls the tank 110 to swing, and any method capable of controlling the tank 110 to swing falls within the scope of the disclosure. For example, the control unit 150 may control the tank 110 to swing when the forming platform 120 rises to a certain height, such as higher than the liquid surface S1 of the uncured liquid forming material 102.

Next, in Step S202, the control unit 150 detects the wave motion of the liquid forming material 102 to obtain detection waveform information of the liquid forming material 102. More specifically, the control unit 150 detects the wave motion of the liquid forming material 102 through the detection unit 140. When the wave motion is generated on the liquid surface S1 of the liquid forming material 102 due to the shaking of the tank 110, the floating module 143 swings with the wave motion on the liquid surface S1. Accordingly, the control unit 150 obtains the detection waveform information of the liquid forming material 102 based on the swing of the floating module 143. The detection waveform information indicates a state of the wave motion on the liquid surface S1.

Thereafter, in Step S203, the control unit 150 compares the detection waveform information of the liquid forming material 102 with sample waveform information to obtain a characteristic comparison result in association with the liquid forming material 102. The sample waveform information is data established in a database and may be standard data obtained through experiments and tests on various liquid forming materials before performing printing. It should be noted that a method by which the control unit 150 controls the tank 110 to swing during a process of establishing the sample waveform information through experiments and tests is the same as the method by which the control unit 150 controls the tank 110 to swing in Step S201. Therefore, the detection waveform information and the sample waveform information, generated based on the same conditions, can be compared with each other.

Then, in Step S204, the control unit 150 executes a predefined operation according to the characteristic comparison result. In the embodiment of the disclosure, the predefined operation may be issuing an alarm, stopping printing the three-dimensional object, or adjusting at least one control parameter, and the three-dimensional printing apparatus prints the three-dimensional object according to the adjusted control parameter. That is, the control unit 150 determines whether the liquid forming material 102 in the tank 110 is the material expected by the user according to the characteristic comparison result. Simply put, if a difference between the detection waveform information and the sample waveform information is overly large, the control unit 150 determines that the liquid forming material 102 in the tank 110 is not the material expected by the user and issues an alarm or stops printing the three-dimensional object.

It should be noted that the control unit 150 controls each component of the three-dimensional printing apparatus 10 to perfo the printing operation according to many control parameters. More specifically, these control parameters may be a movement speed of the forming platform 120 or a movement distance corresponding to one single cut layer object. The control parameters may also be irradiation intensity or a scan speed of the light source 130, or a movement speed and a movement direction of the tank 110. The disclosure is not intended to limit the type of the control parameters. Accordingly, when the control unit 150 determines that the liquid forming material 102 has changed with time according to the characteristic comparison result, the control unit 150 adjusts the various control parameters to improve the printing quality.

Figure 3:
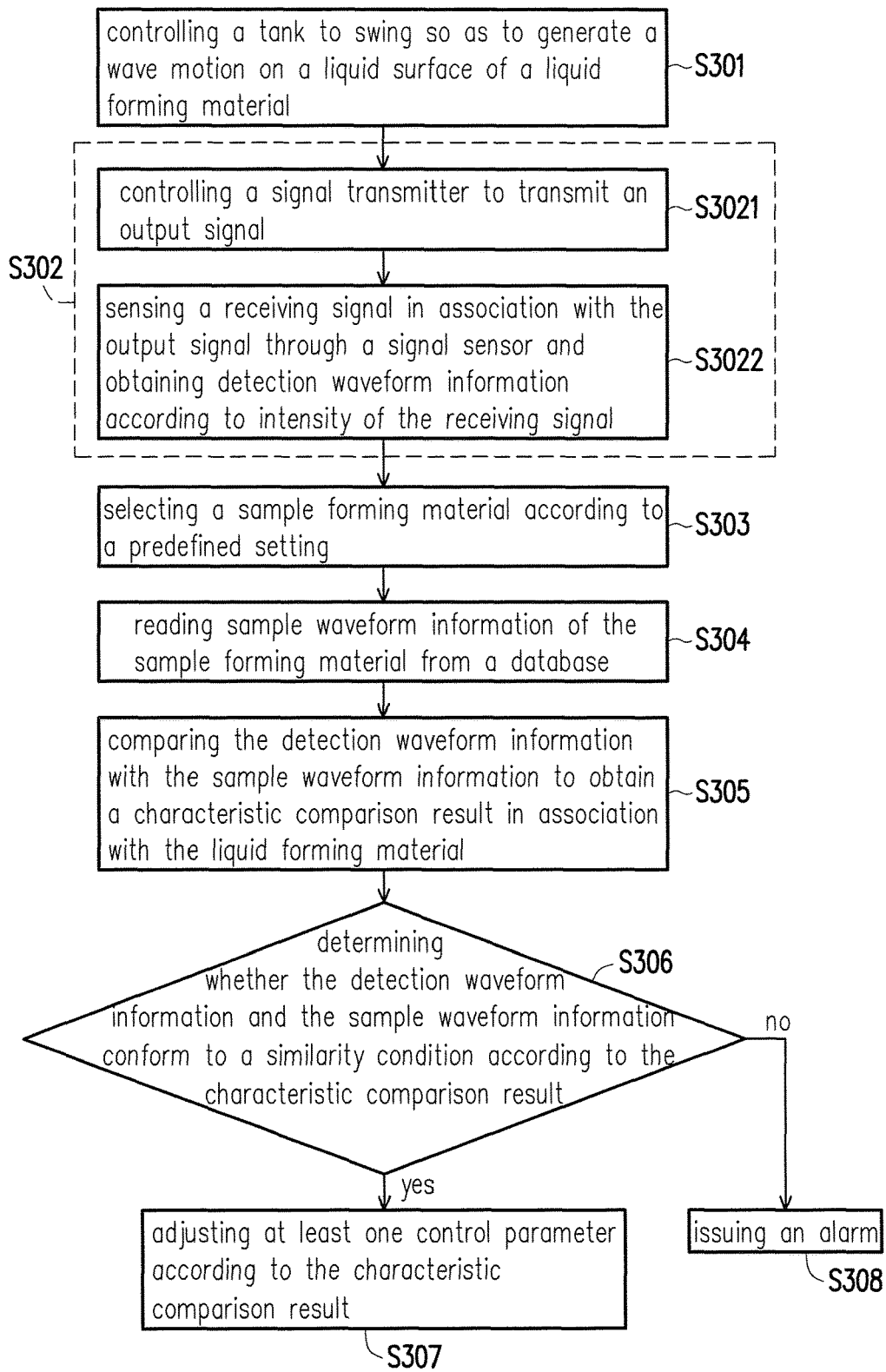
FIG. 3 is a flowchart illustrating a method for detecting a characteristic of a forming material according to an exemplary embodiment.

In order to further explain the disclosure, FIG. 3 provides a flowchart illustrating a method for detecting a characteristic of a forming material according to an exemplary embodiment. The method for detecting the characteristic of the forming material in this embodiment is adapted for the three-dimensional printing apparatus 10 of FIG. 1. Steps of this embodiment are explained in detail hereinafter with reference to the components and modules of the three-dimensional printing apparatus 10. Please refer to FIG. 1 and FIG. 3.

In Step S301, the control unit 150 controls the tank 110 to swing, so as to generate a wave motion on the liquid surface S1 of the liquid forming material 102. In Step S302, the control unit 150 detects the wave motion of the liquid forming material 102 to obtain the detection waveform information of the liquid forming material 102. In this embodiment, Step S302 may be divided into Step S3021 and Step S3022. In Step S3021, the control unit 150 controls the signal transmitter 141 to transmit the output signal E. In Step S3022, the control unit 150 senses the receiving signal R in association with the output signal E through the signal sensor 142 and obtains the detection waveform information according to the intensity of the receiving signal R, wherein the intensity of the receiving signal R changes with an amplitude of the swing of the floating module 143.

It should be noted that the method for obtaining the detection waveform information according to the intensity of the receiving signal R may be implemented differently according to the positions of the signal transmitter 141 and the signal sensor 142. Two examples are given below to explain the disclosure.

Figure 4A:
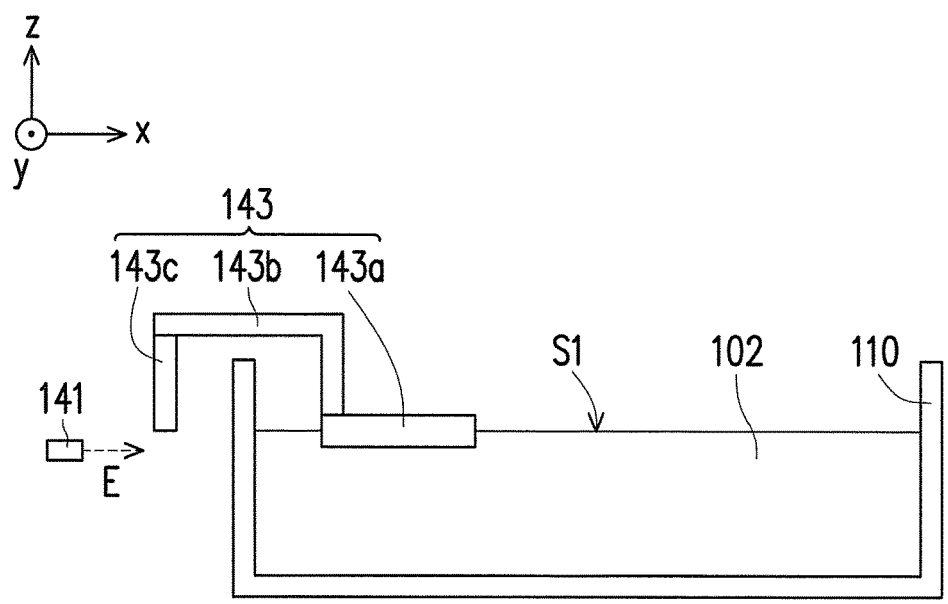
FIG. 4A is a partial lateral view of a three-dimensional printing apparatus according to an exemplary embodiment.
Figure 4B:
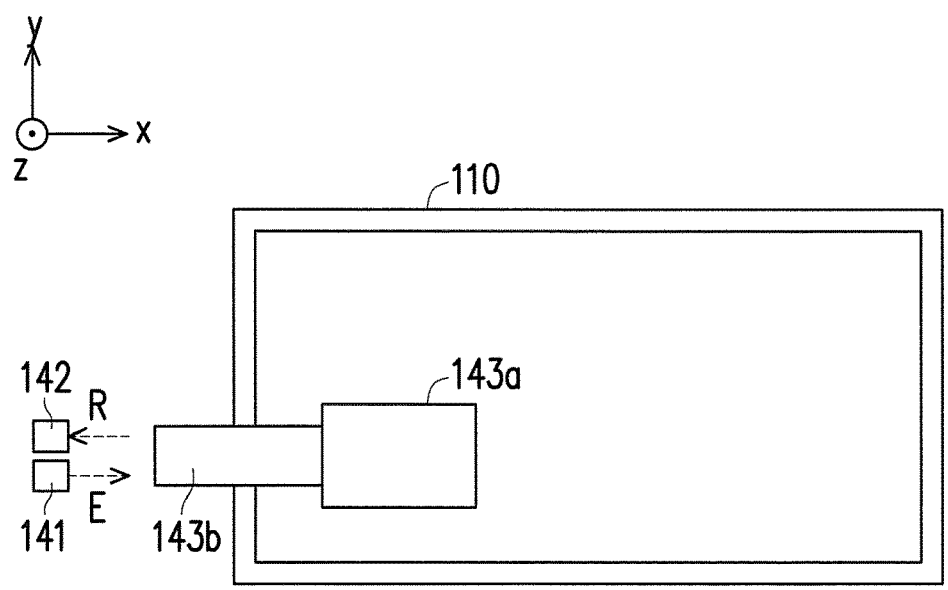
FIG. 4B is a partial top view of a three-dimensional printing apparatus according to an exemplary embodiment.

FIG. 4A is a partial lateral view of a three-dimensional printing apparatus according to an exemplary embodiment. FIG. 4B is a partial top view of a three-dimensional printing apparatus according to an exemplary embodiment. With reference to FIG. 4A and FIG. 4B, in this example, the floating module 143 includes a floating body 143a, a linkage module 143b, and a baffle 143c, wherein the linkage module 143b connects the floating body 143a and the baffle 143c. The floating body 143a is a floating ball filled with air or a floating plate having a relatively small density value, for example, and the floating body 143a is adapted to float on the liquid surface S1. The signal transmitter 141 and the signal sensor 142 are disposed at the same side of the baffle 143c. The signal transmitter 141 transmits the output signal E in a direction toward the baffle 143c, and the receiving signal R is generated by reflection of the output signal E by the baffle 143c. The signal sensor 142 is configured to sense the intensity of the receiving signal R.

More specifically, when the entirety of the floating module 143 swings due to the wave motion on the liquid surface S1, the baffle 143c also swings up and down with the wave motion on the liquid surface S1. As the baffle 143c swings up and down, the baffle 143c may reflect the output signal E completely or reflect only part of the output signal E. Therefore, the intensity of the receiving signal R, generated by reflection of the output signal E, changes with the swing of the baffle 143c. Thus, the signal sensor 142 senses the receiving signal R with different intensities as the floating module 143 swings, and the control unit 150 establishes the detection waveform information of the liquid forming material 102 based on the intensity of the receiving signal R. More specifically, the signal sensor 142 generates a voltage corresponding to the intensity of the receiving signal R, and a continuous detection waveform is established on a time line according to the voltage outputted by the signal sensor 142 to serve as the detection waveform information.

Figure 5A:
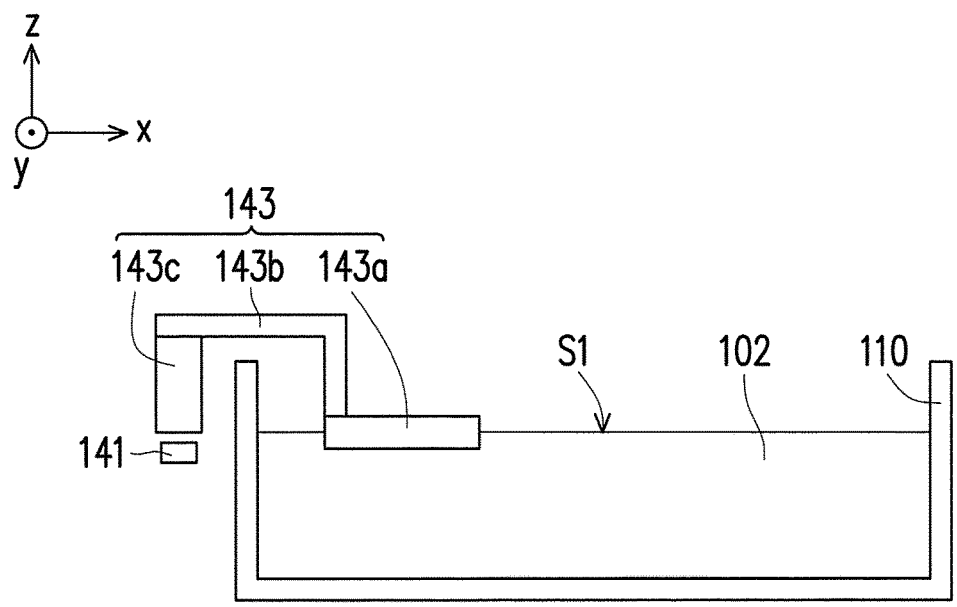
FIG. 5A is a partial lateral view of a three-dimensional printing apparatus according to an exemplary embodiment.
Figure 5B:
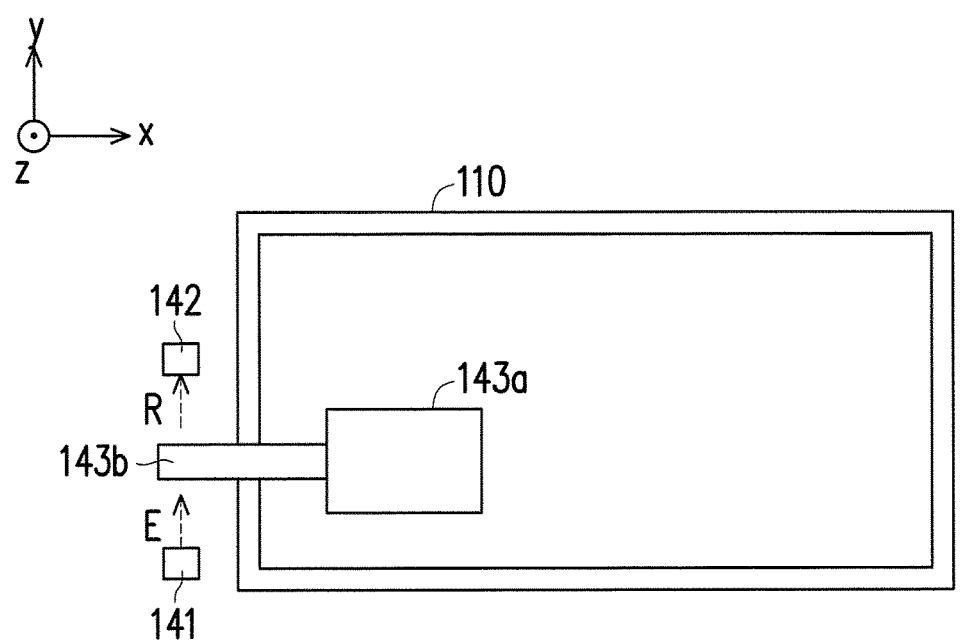
FIG. 5B is a partial top view of a three-dimensional printing apparatus according to an exemplary embodiment.

On the other hand, FIG. 5A is a partial lateral view of a three-dimensional printing apparatus according to an exemplary embodiment. FIG. 5B is a partial top view of a three-dimensional printing apparatus according to an exemplary embodiment. With reference to FIG. 5A and FIG. 5B, in this example, the floating module 143 includes the floating body 143a, the linkage module 143b, and the baffle 143c, wherein the linkage module 143b connects the floating body 143a and the baffle 143c. In this example, the signal transmitter 141 and the signal sensor 142 are disposed at different sides of the baffle 143c. The signal transmitter 141 transmits the output signal E in a direction toward the baffle 143c. The output signal E that is not blocked by the baffle 143c becomes the receiving signal R to be sensed by the signal sensor 142. It is known that, in this example, the receiving signal R is the output signal.

More specifically, when the entirety of the floating module 143 swings with the wave motion on the liquid surface S1, the baffle 143c also swings up and down with the wave motion on the liquid surface S1. As the baffle 143c swings up and down, the baffle 143c may block the output signal E completely or block only part of the output signal E. Therefore, the intensity of the receiving signal R changes with the swing of the baffle 143c. Thus, the signal sensor 142 at the other side of the baffle 143c senses the receiving signal R with different intensities as the floating module 143 swings, and the control unit 150 establishes the detection waveform information of the liquid forming material 102 based on the intensity of the receiving signal R. Similarly, the signal sensor 142 generates a voltage corresponding to the intensity of the receiving signal R, and a continuous detection waveform is established on a time line according to the voltage outputted by the signal sensor 142 to serve as the detection waveform information.

In Step S303, the control unit 150 selects a correct sample forming material according to a predefined setting. The predefined setting may be determined by the user's input or a predetermined value. However, the disclosure is not limited thereto. In Step S304, the control unit 150 reads sample waveform information of the sample forming material from the database. More specifically, the sample waveform information of various types of liquid forming materials have been established in the database through tests and experiments that are performed in advance.

Thereafter, in Step S305, the control unit 150 compares the detection waveform information with the sample waveform information to obtain the characteristic comparison result in association with the liquid forming material 102. To be more specific, the control unit 150 compares the detection waveform information and the sample waveform information according to a frequency parameter, an amplitude parameter, or an endpoint number of the detection waveform information to obtain a frequency comparison result, an amplitude comparison result, or an endpoint comparison result of the characteristic comparison result. Thus, the control unit 150 determines whether the liquid forming material 102 deteriorates or whether the liquid forming material 102 is not the material the user expects according to the frequency comparison result, the amplitude comparison result, or the endpoint comparison result of the characteristic comparison result.

Figure 6:
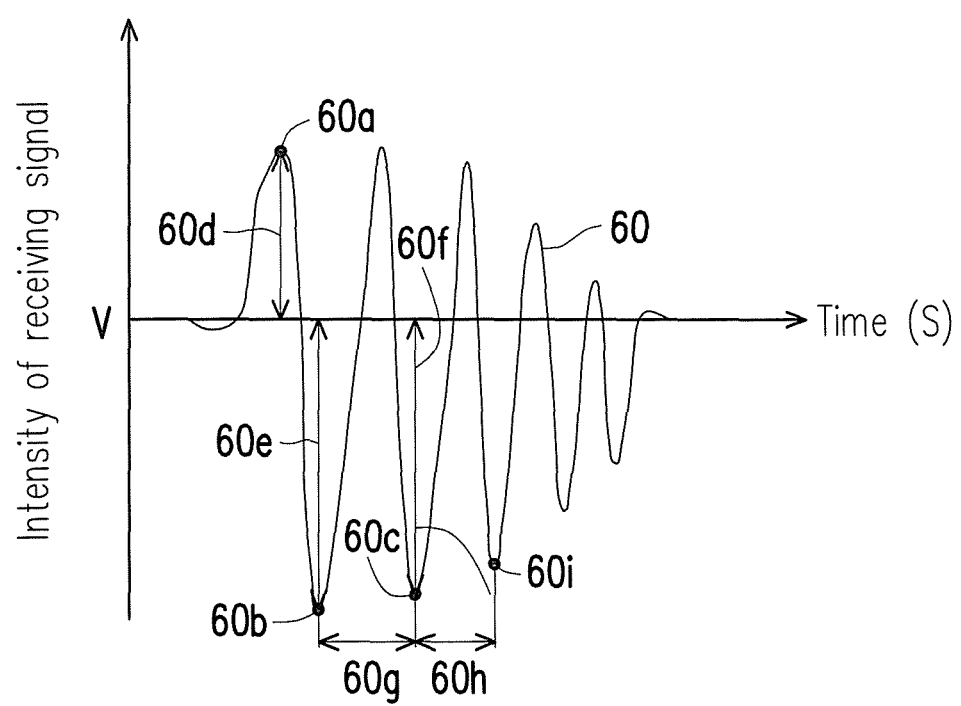
FIG. 6 illustrates an example of detection waveform information according to an exemplary embodiment.

To further explain the disclosure, FIG. 6 illustrates an example of detection waveform information according to an exemplary embodiment. With reference to FIG. 6, the horizontal axis is a time axis and the vertical axis indicates a physical meaning, i.e. the intensity of the receiving signal R. A detection waveform 60 is the detection waveform information that the control unit 150 obtains through the detection unit 140. When the intensity of the receiving signal stays being a value V, it indicates that the liquid surface S1 of the liquid forming material 102 is in a static state and has not wave motion. The detection waveform 60 includes a plurality of peaks and valleys, which are endpoints of the detection waveform 60. For example, the detection waveform 60 includes an endpoint 60a, an endpoint 60b, an endpoint 60c, and an endpoint 60i.

As shown in FIG. 6, the endpoint 60a has a corresponding amplitude parameter 60d, the endpoint 60b has a corresponding amplitude parameter 60e, and the endpoint 60c has a corresponding amplitude parameter 60f. Accordingly, each endpoint has one corresponding amplitude parameter, which is equal to a difference between the endpoint and the value V. In addition, two adjacent endpoints have a corresponding frequency parameter therebetween. For example, a time difference between the endpoint 60b and the endpoint 60c may serve as a frequency parameter 60g, and a time difference between the endpoint 60c and the endpoint 60i may serve as a frequency parameter 60h. To sum up, the detection waveform 60 has a plurality of amplitude parameters and frequency parameters. Moreover, a total of the endpoints of the detection waveform 60 is the endpoint number.

Based on the above, the control unit 150 compares the detection waveform 60 and the sample waveform information according to the frequency parameter, the amplitude parameter, or the endpoint number of the detection waveform 60, and determines whether the detection waveform 60 is the same as or similar to the sample waveform information according to the frequency comparison result, the amplitude comparison result, or the endpoint comparison result obtained through the comparison. It should be noted that the frequency parameter, the amplitude parameter, or the endpoint number of the detection waveform 60 is associated with the detected material characteristic of the liquid forming material. For example, for a liquid forming material with higher viscosity, the time difference between the endpoints is longer. Thus, by comparing the detection waveform information obtained through detection and the sample waveform information in the database, the three-dimensional printing apparatus 10 determines whether the liquid forming material 102 deteriorates or is used incorrectly.

Then, reverting to the flowchart of FIG. 3, in Step S306, the control unit 150 determines whether the detection waveform information and the sample waveform information conform to a similarity condition according to the characteristic comparison result. Simply put, the control unit 150 determines the similarity between the detection waveform information and the sample waveform information according to the characteristic comparison result generated by comparison of the detection waveform information and the sample waveform information.

Figure 7:
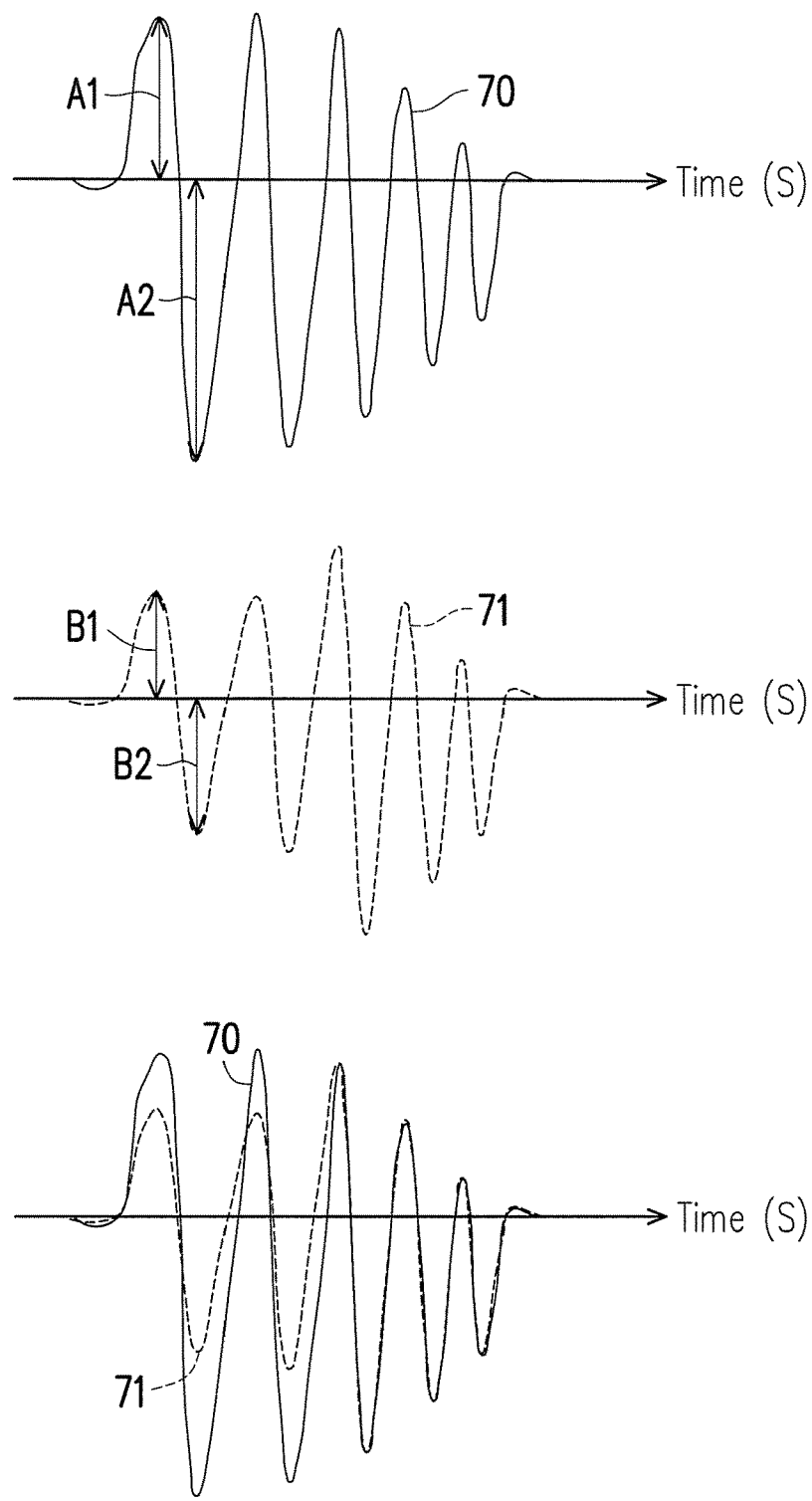
FIG. 7 illustrates examples of comparison between detection waveform information and sample waveform information according to an exemplary embodiment.

For example, FIG. 7 illustrates examples of comparison between detection waveform information and sample waveform information according to an exemplary embodiment. With reference to FIG. 7, it is given that a sample waveform 70 is the sample waveform information and a detection waveform 71 is the detection waveform information. The sample waveform 70 includes an amplitude parameter A1 and an amplitude parameter A2, and the detection waveform 71 includes an amplitude parameter B1 and an amplitude parameter B2. The control unit 150 compares the amplitude parameter A1 with the amplitude parameter B1, and compares the amplitude parameter A2 with the amplitude parameter B2. In this example, because a difference between the amplitude parameter A1 and the amplitude parameter B1 and a difference between the amplitude parameter A2 and the amplitude parameter B2 are overly large, the control unit 150 determines that the detection waveform information and the sample waveform information do not conform to the similarity condition. For example, the control unit 150 may determine whether the difference between the amplitude parameter A1 and the amplitude parameter B1 is larger than a predefined threshold value to decide whether the difference between the amplitude parameter A1 and the amplitude parameter B1 is overly large.

Figure 8:
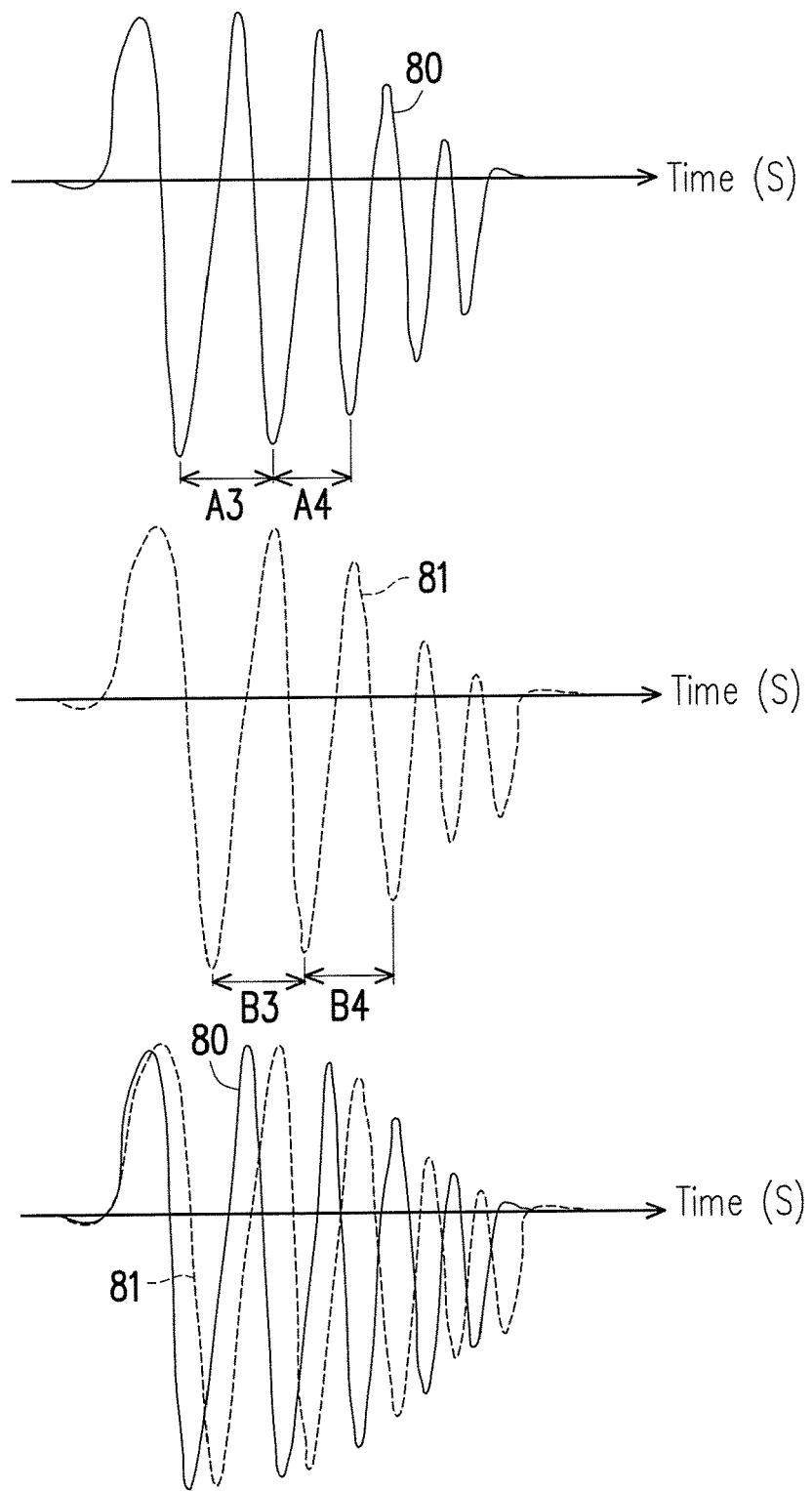
FIG. 8 illustrates examples of comparison between detection waveform information and sample waveform information according to an exemplary embodiment.

Further, FIG. 8 illustrates examples of comparison between detection waveform information and sample waveform information according to an exemplary embodiment. With reference to FIG. 8, it is given that a sample waveform 80 is the sample waveform information and a detection waveform 81 is the detection waveform information. The sample waveform 80 includes a frequency parameter A3 and a frequency parameter A4, and the detection waveform 81 includes a frequency parameter B3 and a frequency parameter B4. The control unit 150 compares the frequency parameter A3 with the frequency parameter B3, and compares the frequency parameter A4 with the frequency parameter B4. In this example, because the frequency parameter A3 differs from the frequency parameter B3 and the frequency parameter A4 differs from the frequency parameter B4, the control unit 150 determines that the detection waveform information and the sample waveform information do not conform to the similarity condition. For example, the control unit 150 may determine whether a difference between the frequency parameter A1 and the frequency parameter B1 is larger than a predefined threshold value to decide whether the frequency parameter A3 differs from the frequency parameter B3. However, it should be noted that FIG. 7 and FIG. 8 are merely examples, and the disclosure is not limited thereto. Those skilled in the art may determine the comparison method based on the frequency parameter, the amplitude parameter, and the endpoint number according to their actual needs. Thus, details will not be repeated here.

Further to the above, when the detection waveform information and the sample waveform information conform to the similarity condition, it indicates that the detection waveform information is similar to the sample waveform information. If the detection waveform information is similar to the sample waveform information, it indicates that the liquid forming material 102 is the material expected by the user. Nevertheless, it is noted that, even if the situation of using wrong liquid forming material 102 does not occur, the characteristic of the liquid forming material 102 may change with time. In that case, the control unit 150 may obtain a degree of change of the liquid forming material 102 according to the characteristic comparison result. Therefore, if the result of Step S306 is YES, in Step S307, the control unit 150 may adjust at least one control parameter of the three-dimensional printing apparatus 10 according to the characteristic comparison result to improve the printing quality.

In addition, if the detection waveform information and the sample waveform information do not conform to the similarity condition, it indicates that the difference between the detection waveform information and the sample waveform information is overly large. When the difference between the detection waveform information and the sample waveform information is overly large, it indicates that the liquid forming material 102 is not the material expected by the user. Thus, if the result of Step S306 is NO, in Step S308, the control unit 150 issues an alarm. The control unit 150 may control the three-dimensional printing apparatus 10 to output one of an indicating text, a sound, and a lamplight, or an alarm of a combination of the foregoing, so as to remind the user of incorrect use or serious deterioration of the liquid forming material 102 in the tank 10.

To conclude, in the embodiments of the disclosure, the three-dimensional printing apparatus detects the wave motion on the liquid surface of the liquid forming material through the detection unit, thereby obtaining the detection waveform information indicative of the current material characteristic. Further, the three-dimensional printing apparatus obtains the characteristic comparison result by comparing the detection waveform information with the sample waveform information in the database, and adjusts the control parameter for printing the three-dimensional object based on the characteristic comparison result, so as to improve the quality of three-dimensional printing. In addition to the above, the three-dimensional printing apparatus determines whether the liquid forming material in the tank is the material expected by the user according to the characteristic comparison material, so as to prevent printing failure. Therefore, the disclosure improves the practicality of the three-dimensional printing apparatus in use and operation and prevents wasting the printing material to reduce the costs.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A detecting method for detecting a characteristic of a forming material, the detecting method being adapted for a three-dimensional printing apparatus that comprises a control unit, a detection unit and a tank filled with a liquid forming material and a light source disposed at one side of the tank to irradiate the liquid forming material, and the detecting method comprising:
controlling, by the control unit, the tank of the three-dimensional printing apparatus to swing to generate a wave motion on a liquid surface of the liquid forming material;
detecting, by the detection unit, the wave motion of the liquid forming material to obtain detection waveform information;
comparing, by the control unit, the detection waveform information with sample waveform information to obtain a characteristic comparison result in association with the liquid forming material; and
executing a predefined operation according to the characteristic comparison result, wherein the predetermined operation comprises adjusting at least one control parameter, and the three-dimensional printing apparatus prints a three-dimensional object according to the at least one control parameter.

2. The detecting method according to claim 1, wherein the predefined operation further comprises issuing an alarm and stopping printing a three-dimensional object.

3. The detecting method according to claim 1, wherein the three-dimensional printing apparatus further comprises a forming platform, wherein the light source irradiates and cures the liquid forming material between the forming platform and a bottom of the tank, and the step of controlling the tank to swing to generate the wave motion on the liquid surface of the liquid forming material comprises:
controlling the tank to move to separate the liquid forming material that has been cured from the bottom of the tank and to cause the tank to swing.

4. The detecting method according to claim 1, wherein the three-dimensional printing apparatus further comprises a detection unit disposed at a side of the tank, wherein the detection unit comprises a signal transmitter and a signal sensor, and the step of detecting the wave motion of the liquid forming material to obtain the detection waveform information comprises:
controlling the signal transmitter to transmit an output signal; and
sensing a receiving signal in association with the output signal through the signal sensor and obtaining the detection waveform information according to intensity of the receiving signal, wherein the receiving signal is the output signal or a reflected signal of the output signal.

5. The detecting method according to claim 4, wherein the detection unit further comprises a floating module adapted to float on the liquid surface of the liquid forming material and swing with the wave motion of the liquid forming material, wherein the signal transmitter transmits the output signal toward the floating module and the intensity of the receiving signal changes with an amplitude of the swing.

6. The detecting method according to claim 1, wherein, before the step of comparing the detection waveform information with the sample waveform information to obtain the characteristic comparison result in association with the liquid forming material, the detecting method further comprises:
selecting a sample forming material according to a predefined setting; and
reading the sample waveform information of the sample forming material from a database.

7. The detecting method according to claim 1, wherein the step of comparing the detection waveform information with the sample waveform information to obtain the characteristic comparison result in association with the liquid forming material comprises:
comparing the detection waveform information with the sample waveform information according to a frequency parameter, an amplitude parameter, or an endpoint number of the detection waveform information to obtain a frequency comparison result, an amplitude comparison result, or an endpoint comparison result of the characteristic comparison result.

8. The detecting method according to claim 1, wherein, after the step of comparing the detection waveform information with the sample waveform information to obtain the characteristic comparison result in association with the liquid forming material, the detecting method further comprises:
determining whether the detection waveform information and the sample waveform information conform to a similarity condition according to the characteristic comparison result.

9. The detecting method according to claim 1, wherein the three-dimensional printing apparatus is a SL (stereolithography) three-dimensional printing apparatus.

* * * * *